United States Patent
Dearnaley et al.

(10) Patent No.: US 6,306,175 B1
(45) Date of Patent: Oct. 23, 2001

(54) TITANIUM ALLOY HIP PROSTHESIS

(75) Inventors: Geoffrey Dearnaley, Abingdon; Alan Thomas Peacock, Wantage, both of (GB)

(73) Assignee: AEA Technology plc, Harwell (GB)

( * ) Notice: Subject to any disclaimer, the term of this patent is extended or adjusted under 35 U.S.C. 154(b) by 0 days.

(21) Appl. No.: 08/395,285

(22) Filed: Feb. 27, 1995

Related U.S. Application Data

(63) Continuation of application No. 07/978,966, filed on Nov. 23, 1992, now abandoned, which is a continuation of application No. 07/611,466, filed on Oct. 9, 1990, now abandoned, which is a continuation of application No. 07/179,265, filed on Apr. 8, 1988, now abandoned, which is a continuation of application No. 06/884,030, filed on Jul. 10, 1986, now abandoned, which is a continuation of application No. 06/624,294, filed on Jun. 25, 1984, now abandoned.

(30) Foreign Application Priority Data

Feb. 28, 1984 (GB) .................................................. 8405170

(51) Int. Cl.$^7$ ....................................................... A61F 2/36
(52) U.S. Cl. ..................................... 623/23.11; 623/18.11
(58) Field of Search ................................ 623/22, 16, 18

(56) References Cited

U.S. PATENT DOCUMENTS

| | | | |
|---|---|---|---|
| 3,583,361 | * 6/1971 | Laudel, Jr. | 118/6 |
| 3,953,619 | * 4/1976 | Matsubara | 427/39 |
| 4,346,123 | * 8/1982 | Kaufmann | 427/38 |
| 4,365,359 | * 12/1982 | Raab | 623/22 |
| 4,401,719 | * 8/1983 | Kobayashi et al. | 428/457 |
| 4,465,524 | * 8/1984 | Dearnaley et al. | 428/660 |
| 4,466,991 | * 8/1984 | Andreev et al. | 427/38 |

OTHER PUBLICATIONS

Oliver et al., "The Wear Behavior of Nitrogen Implanted Metals", Met. Trans., vol. 15A, p. 2221–2229, Dec., 1984.*

* cited by examiner

*Primary Examiner*—Mickey Yu
*Assistant Examiner*—John M. Black
(74) *Attorney, Agent, or Firm*—William H. Holt

(57) ABSTRACT

A femoral component as herein before described for an artificial hip joint made out of an alloy containing titanium, wherein at least a major load bearing portion of which has been subjected to bombardment by a beam of nitrogen or other light ions having energies in the range of 10 Kev to 200 Kev until a surface fluence of between 1 and $8 \times 10^{17}$ ions/cm$^2$ has been implanted. An apparatus for processing such components is described also.

16 Claims, 2 Drawing Sheets

TITANIUM ALLOY HIP PROSTHESIS

Figure 1:
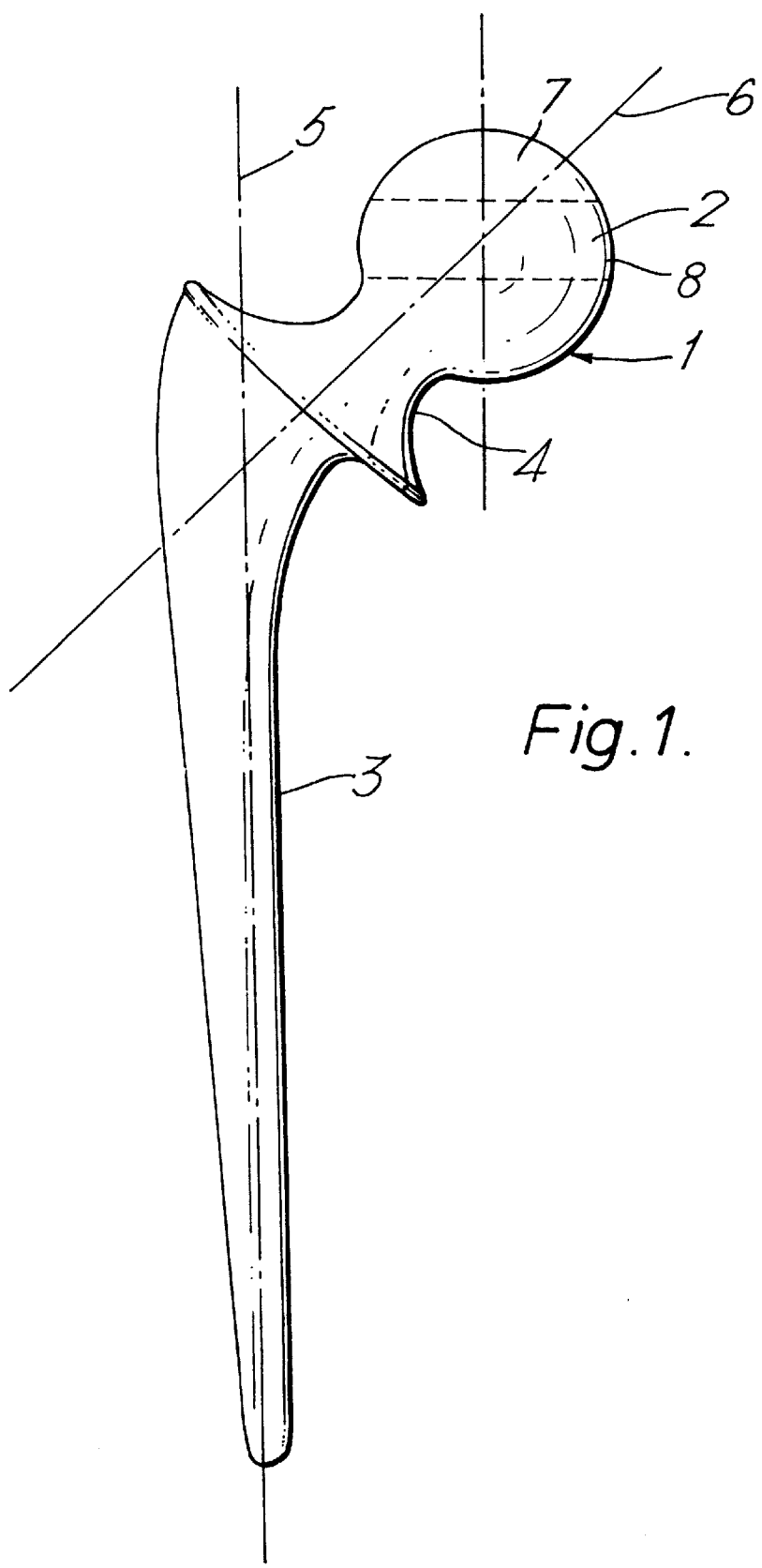

This is a continuation of application Ser. No. 07/978,966 filed Nov. 23, 1992, which is a continuation of application Ser. No. 07/611,466 filed Oct. 9, 1990, now abandoned, which is a continuation of Ser. No. 07/179,265 filed Apr. 8, 1988, now abandoned, which is a continuation of Ser. No. 06/884,030 filed Jul. 10, 1986, now abandoned, which is a continuation of Ser. No. 06/624,294 filed Jun. 25, 1984, now abandoned.

The present invention relates to artificial hip joints consisting of a femoral component consisting of a spherical head attached at an appropriate angle to a shank by means of which it can be attached to the upper end of a femur belonging to a patient who is to receive the hip joint, and a bearing cup, called the acetabular cup which is attached to the associated end of the pelvis of the patient.

In total hip replacements, a preferred material for the femoral component is a titanium alloy because of its high corrosion resistance, good tensile strength and fatigue resistance. The acetabular cup preferably is made of a plastics material, ultra high molecular weight polyethylene being a particularly suitable material.

However, wear debris from these components can cause inflammation of local tissue and a susceptibility to infection which may, in turn, lead to attack of the bones and the loosening of the prosthesis, particularly the femoral component. Also, abrasive wear of the femoral component can take place to such an extent that it commences to gouge the acetabular cup, creating massive particles of polymeric debris.

According to the present invention there is provided a femoral component as herein before described for an artificial hip joint made out of an alloy containing titanium, wherein at least a major load bearing portion of which has been subjected to bombardment by a beam of nitrogen or other light ions having energies in the range of 10 Kev to 200 Kev until a surface fluence of between 1 and $8 \times 10^{17}$ ions/cm$^2$ has been implanted. Light ions are considered to be at least nitrogen, carbon, boron, or neon as is set out in the abstract of our U.S. Pat. No. 4,465,524, granted on Aug. 14, 1984, the teachings being incorporated herein by reference.

Preferably the ion implantation is carried out in such a way that the surface fluence over the said load-bearing portion of the femoral compound varies in the same way as the expected load when the femoral component is in use.

Also according to the invention there is provided an apparatus for carrying out the process of implantation of the nitrogen ions or other light ions, comprising a chamber, means for evacuating the chamber, a carriage adapted to carry a plurality of femoral components as hereinbefore described of an artificial hip joint one behind the other with the direction of offset of the heads of the femoral components parallel to the direction of movement of the carriage, a plurality of ion sources so positioned that the region of the heads of the femoral components which in use will bear the maximum load receive a maximum surface fluence of ions, and the region of minimum load receives a minimum surface fluence of ions, and means for moving the carriage past the ion sources.

Preferably, the temperature of the heads of the femoral components during the implantation of the nitrogen ions is some 300° C. This may be achieved as a result of the implantation process, or the femoral components can be heated to the required temperature. Furthermore, preferably there is provided in the chamber trace amounts of a carbon-containing gas or vapour. At the temperature indicated above, carbon impinging on the surfaces of the heads of the femoral components will be able to penetrate the metal where it augments the hardening action of the implanted nitrogen. An advantageous concentration of carbon is half that of the implanted nitrogen. A suitable way of providing the carbon is to use as the means for evacuating the chamber a vacuum pump utilising a hydrocarbon oil. A residual pressure of about $5 \times 10^{-5}$ torr will then provide the required carbon concentration.

Figure 2:
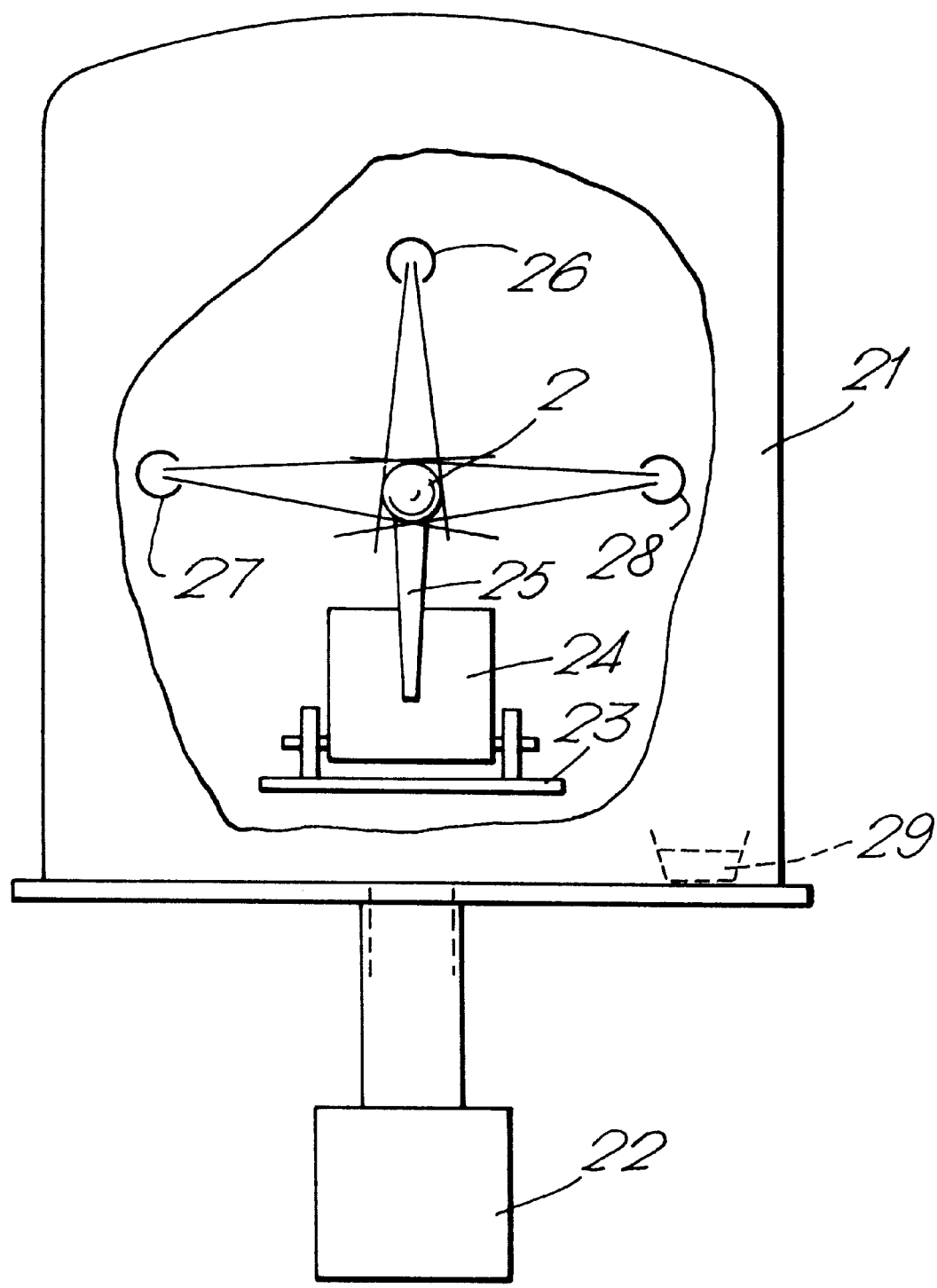

The invention will now be described, by way of example, with reference to the accompanying drawings, in which, FIG. 1 is a view of a femoral component of an artificial hip joint, and FIG. 2 is a diagrammatic representation of a machine for performing the invention.

Referring to FIG. 1, a femoral component of an artificial hip joint consists of a head 1 in the form of a ball 2 of some 32 mm diameter, which is attached by means of a neck 4 to a shank 3 adapted to be inserted into a femur of a patient. The ball 2 is offset from the longitudinal axis 5 of the shank 3, and the longitudinal axis 6 of the neck 4 is at an angle of some 45° to that of the shank 3.

Although the amount of offset of the ball 2 from the longitudinal axis 5 of the shank 3 and the diameter of the ball 2 will vary according to the size of the femoral component of the hip joint, which in turn is chosen to match the size of the pelvis and femur of the patient, the angle between the longitudual axis 5 and 6 of the shank 3 and neck 4 does not differ.

The femoral component is made of a titanium alloy containing 6% by weight of aluminium and 4% by weight of vanadium.

The ball 2 is implanted with a surface fluence in the range 4 to $7 \times 10^{17}$ ions/cm$^2$ in a region 7 defined by a cone angle of about 60° from the direction which corresponds to that of maximum load when the femoral component is in its working position. Over the region 8 between the region 7 and a similar one 9 symmetrically disposed in the lower hemisphere of the ball 2, the surface fluence is in the range 2 to $4.7 \times 10^{17}$ ions/cm$^2$. Little or no ion implantation is required in the region 9.

Referring to FIG. 2, a machine for carrying out the nitrogen implantation consists of a chamber 21 which is connected to an evacuating system shown diagrammatically as 22. Within the chamber 21 is a track 23 for a carriage 24. The carriage is adapted to be moved along the track 23 by any convenient mechanism, which is not illustrated. The carriage 24 is adapted to carry a number of femoral components 25 one behind the other in the same relative positions with the direction of offset of their heads parallel to the direction of motion of the carriage 24. Three cylindrical nitrogen ion sources, 26, 27 and 28 are positioned with their longitudinal axes parallel to the track 23. The source 26 is positioned vertically above the centre line of the track 23, while the ion sources 27 and 28 are positioned so that they are slightly above the centres of the balls 2 as they pass by them. Thus the upper region 7 of each of the balls 2 will receive ions from all three sources, each side of the central region 8 will receive ions from one ion source only, and very few ions will impinge on the region 9.

A receptacle 29 for a quantity of a hydrocarbon coil may be provided to provide a concentration of carbon-containing gaseous vapour in the chamber 21. Alternatively, the evacuating system 22 may be adapted to provide the said vapour.

Thus, the distribution of the surface fluence of nitrogen corresponds to that of the load which will be experienced in use by the head of the femoral component.

Another light ion which can be used is boron.

We claim:

1. A method of producing a femoral component of an artificial hip joint having a spherical head portion attached to an elongated shank, the head portion being made at least primarily of titanium, the method comprising bombarding a surface region of the head portion with light ions having energies in the range 10 to 200 keV until a surface concentration of between 1 and $8 \times 10^{17}$ ions/cm$^2$ have been implanted.

2. A method as claimed in claim 1 wherein the ions are selected from nitrogen and boron.

3. A method as claimed in claim 1 further comprising controlling the bombardment and implantation to vary the concentration of said ions over said head portion.

4. A method of producing a femoral component of an artificial hip joint according to claim 3 wherein the bombardment and implantation are effected by exposing the spherical head portion to a plurality of sources of said ions so arranged that ion beams from the sources overlap in such a way as to provide the varying distribution of the surface concentration of said ions.

5. A method as claimed in claim 3 comprising controlling the bombardment and implantation to vary the concentration of said ions from 4 to $7 \times 10^{17}$ ions/cm$^2$ in the region of maximum loading of the head portion and between 2 and $5.7 \times 10^{17}$ ions/cm$^2$ in less heavily loaded regions of the head portion.

6. A method of producing a femoral component of an artificial hip joint according to claim 5 wherein the ion bombardment is carried out under vacuum conditions at a temperature of at least 300° C. with trace amounts of a carbon-containing gaseous material present.

7. A method producing a femoral component of an artificial hip joint according to claim 6 wherein the carbon-containing gaseous material is a hydrocarbon oil vapour at a pressure of about $5 \times 10^{-5}$ torr.

8. A method of producing a femoral component of an artificial hip joint according to claim 5 wherein the bombardment and implantation are effected by exposing the spherical head portion to a plurality of sources of said ions so arranged that ion beams from the sources overlap in such a way as to provide the varying distribution of the surface concentration of said ions.

9. A method as claimed in claim 5 wherein the region of maximum concentration of implanted ions extends over a cone angle of about 60°.

10. A method as claimed in claim 5 wherein the maximum concentration of implanted ions is in a vertically symmetrical region having a cone angle of about 60°.

11. A femoral component of an artificial hip joint comprising a spherical head portion attached to an elongated shank, wherein the head portion is made at least primarily of titanium and includes a surface region which has been subjected to bombardment with light ions having energies in the range of 10 to 200 keV until a surface concentration of between 1 and $8 \times 10^{17}$ ions/cm$^2$ have been implanted.

12. A femoral component for an artificial hip joint according to claim 11 wherein the surface concentration of sand ions varies over said head portion.

13. A femoral component of an artificial hip joint according to claim 12 wherein the concentration of ions varies from 4 to $7 \times 10^{17}$ ions/cm$^2$ in the region of maximum loading of said head portion and between 2 and $5.7 \times 10^{17}$ ions/cm$^2$ in less heavily loaded regions of said head portion.

14. A femoral component of an artificial hip joint according to claim 13 wherein the region of maximum concentration of implanted ions extends over a cone angle of 60°.

15. A femoral component of an artificial hip joint according to claim 11 wherein said surface concentration of ions includes carbon.

16. A femoral component of an artificial hip joint according to claim 15 wherein the concentration of carbon is approximately half that of said ions.

* * * * *